US008175282B2

(12) United States Patent
Nielsen et al.

(10) Patent No.: US 8,175,282 B2
(45) Date of Patent: May 8, 2012

(54) METHOD OF EVALUATING PERCEPTION INTENSITY OF AN AUDIO SIGNAL AND A METHOD OF CONTROLLING AN INPUT AUDIO SIGNAL ON THE BASIS OF THE EVALUATION

(75) Inventors: Søren Henningsen Nielsen, Lystrup (DK); Esben Skovenborg, Århus C (DK)

(73) Assignee: The TC Group A/S (DK)

( * ) Notice: Subject to any disclaimer, the term of this patent is extended or adjusted under 35 U.S.C. 154(b) by 1533 days.

(21) Appl. No.: 11/630,727

(22) PCT Filed: Jun. 25, 2004

(86) PCT No.: PCT/DK2004/000458

§ 371 (c)(1),
(2), (4) Date: Dec. 21, 2006

(87) PCT Pub. No.: WO2006/000215

PCT Pub. Date: Jan. 5, 2006

(65) Prior Publication Data

US 2008/0031464 A1 Feb. 7, 2008

(51) Int. Cl.
*H04R 29/00* (2006.01)
*A61F 11/06* (2006.01)
*H03G 3/00* (2006.01)

(52) U.S. Cl. ............. 381/56; 381/72; 381/107; 381/108

(58) Field of Classification Search .................... 381/56, 381/107, 108, 72, 312
See application file for complete search history.

(56) References Cited

OTHER PUBLICATIONS

International Search Report; PCT/DK2004/000458; Mar. 2, 2005.
Siegfried Klar, Gerhard Spikofski: "On levelling and loudness problems at television and radio broadcast studios (Convention Paper 5538)" 112TH Convention of the Audio Engineering Society, May 10, 2002, May 13, 2002, pp. 1-17, XP002317487, p. 4, section 4-p. 7, section 5.
Spikofski G et al: "Leveling and loudness—in radio and television broadcasting" EBU Technical Review Eur. Broadcasting Union Switzerland, No. 297, Jan. 2004, XP002317488, ISSN: 1019-6587, p. 6-p. 9.
Earl Vickers: Automatic Long-Term Loudness and Dynamics Matching: 111TH Convention of the Audio Engineering Society, Sep. 21, 2001-Sep. 24, 2001, pp. 1-11, XP002317489 New York, USA.
Fastl H: "Loudness of Running Speech Measured by a Loudness Meter" Acustica, S. Hirzel Verlag, Stuttgart, DE, vol. 71, No. 2, Jun. 1990, pp. 156-158, XP00952134 ISSN: 001-7884.
Skovenborg et al.: "Loudness Assessment of Music and Speech" 116TH Convention of the Audio Engineering Society, May 8, 2004, May 11, 2004, pp. 1-25, XP002317552 Berlin, Germany.
Zwicker: "Procedure for Calculating loudness of temporally variable sounds" J. Acoustic Society of America, vol. 62, Sep. 1997, pp. 675-682, XP008042823.
Soulodre: "Evaluation of Objective Loudness Meters (Convention Paper 6161)" 116TH Convention of the Audio Engineering Society, May 8, 2004, May 11, 2004, pp. 1-12, XP008042756 Berlin, Germany.

*Primary Examiner* — Vivian Chin
*Assistant Examiner* — Douglas Suthers
(74) *Attorney, Agent, or Firm* — Cantor Colburn LLP

(57) ABSTRACT

Method of evaluating perception intensity of an audio input signal (IS) comprising the steps of receiving the audio input signal (IS), estimating a time variant distribution function (TVDF) on the basis of said audio input signal (IS) or a derivative thereof, determining the perception intensity as at least one perception intensity estimate (PIE) on the basis of said estimated time variant distribution function (TVDF). According to the invention perception intensity has been obtained on the basis of a time variant distribution function. Thereby, an advantageous universal and flexible determination of perception intensity is obtained. The universal applicability is basically obtained due to the fact that a distribution function may match and describe audio input signal of very different nature. Thus, according to the invention even speech, music and noise may be evaluated on the basis of a distribution function.

75 Claims, 12 Drawing Sheets

METHOD OF EVALUATING PERCEPTION INTENSITY OF AN AUDIO SIGNAL AND A METHOD OF CONTROLLING AN INPUT AUDIO SIGNAL ON THE BASIS OF THE EVALUATION

FIELD OF THE INVENTION

The invention relates to a method of evaluating perception intensity of an audio signal as stated in claim 1.

BACKGROUND OF THE INVENTION

Perception intensity estimates of audio signals have been the subject of research for decades. Although audio signal processing and acoustic engineering have reached significant progress with respect to different aspects of recording, engineering, storage and reproduction many key issues have been left as they originally were, namely aspects which were to be dealt with on the basis of subjective analysis of the skilled sound engineer. This manual approach to several key issues is, of course, acceptable to the degree that the individual preference of the recipient, i.e. the listener, determines the individual opinion of the quality of the perceived audio signal.

For different purposes it would, however, be advantageous if a more automated approach to the processing of audio signal was possible. One of these purposes is loudness estimates, which relate to the different listeners' perception of how loud a present signal is. An automated loudness estimation of audio signals is highly needed for different purposes such as automatic gain control in relation to broadcasting or, e.g., reproduction of audio signals in a car.

A problem related to measuring of loudness is that it for many years has been well accepted that the loudness perception of an audio signal is not just a straightforward measurement and a subsequent processing of an audio signal to be evaluated.

A more advanced example of loudness estimation is disclosed in US 2004/0044525 A1 where loudness estimation is based on the assumption that loudness of speech must be evaluated differently than other audio signal components. A problem of the disclosed method is that a signal to be evaluated initially must be processed for the purpose of identifying and separating speech components, which is a relatively complicated and processing consuming affair.

It is the object of the invention to obtain a relatively straightforward and universal loudness evaluation and estimation, which may also serve as the basis for automated gain control.

SUMMARY OF THE INVENTION

The invention relates to a method of evaluating perception intensity of an audio input signal (IS) comprising the steps of receiving the audio input signal (IS),
estimating a time variant distribution function (TVDF) on the basis of said audio input signal (IS) or a derivative thereof,
determining the perception intensity as at least one perception intensity estimate (PIE) on the basis of said estimated time variant distribution function (TVDF).

According to the invention a perception intensity has been obtained on the basis of a time variant distribution function, thereby obtaining an advantageous universal and flexible determination of a perception intensity. The universal applicability is basically obtained due to the fact that a distribution function may match and describe audio input signal of very different nature. Thus, according to the invention even speech, music and noise may be evaluated on the basis of a distribution function.

In an embodiment of the invention said estimation of a time variant distribution function (TVDF) refers to the audio input signal (IS).

According to an embodiment of the invention, a time variant distribution function should, preferably, be performed on the basis of the input signal as; in other words, a feed-forward implementation of the invention. Alternatively, the estimation according to the invention may also be performed on the basis of the output signal In an embodiment of the invention said estimation of a time variant distribution function (TVDF) is made on the basis of a modified audio input signal (MIS)

According to an embodiment of the invention, a time variant distribution function should, preferably, be performed on the basis of the actually modified audio input signal; in other words, a feed-back implementation of the invention.

In an embodiment of the invention said audio input signal comprises a sequence of input samples (IS).

According to a preferred embodiment of the invention, establishment of one perception intensity estimate in the form of a sample should be made on the basis of several audio input signal representative samples, preferably at least two, in order to benefit from the signal history.

In an embodiment of the invention said perception intensity estimate comprises an output sample.

In an embodiment of the invention said time variant distribution function (TVDF) is estimated by a shape description of a distribution function.

Basically, according to the invention a shape should facilitate utilization of not just only a simple representation or single point of such distribution but rather a representation representing the variation of the distribution function. In this specific context variation should not be regarded as a strict mathematical expression, e.g. only variance, but rather reflect the fact that the shape of a distribution function may vary and that this variation may be estimated for the purpose of obtaining an advantageous evaluation of perception intensity. In this context it should also be stressed that a shape description may also comprise parameters or measures, which may not specifically relate to a specific point of the distribution function. On the other hand, such parameters or measures should of course be derived from the distribution function.

Note that the shape refers to a time variant distribution function and thus also comprises a location and a scale. Consequently the shape may form a basis for derival or direct extraction of relevant feature parameters of the time variant distribution function.

In an embodiment of the invention said time variant distribution comprises an amplitude distribution function.

In an embodiment of the invention said time variant distribution comprises a power distribution function.

In an embodiment of the invention said time variant distribution comprises a sound intensity distribution function.

In an embodiment of the invention said time variant distribution comprises a two-dimensional distribution function.

In an embodiment of the invention the determining of the perception intensity estimate (PIE) is made on the basis of at least two time variant distribution functions (TVDF) estimated at least two different times.

In an embodiment of the invention the determining of the perception intensity representative output samples (OS) is on the basis of a weighted accumulation of at least two time variant distribution functions (TVDF) estimated at least two different times.

According to a preferred embodiment of the invention, the estimated time variant distribution function (TVDF) should be weighted over time in order to facilitate the desired derivation of perception intensity. This feature is particular strong when the perception intensity to be determined relates to a loudness estimate.

In an embodiment of the invention an output sample (OS) is determined on the basis of a least two audio input samples (IS)

According to a preferred embodiment of the invention an output sample should, preferably, be based on at least two input samples, thereby obtaining an advantageous description of an input signal, which may broadly be applied for the derivation of a perceptual intensity of representations of audio signals of very different nature.

In an embodiment of the invention the determining of the perception intensity on the basis of said estimated time variant distribution function (TVDF) is done according to at least one non-linear function (NLF).

According to an advantageous embodiment of the invention, a loudness estimate is based on the basis of determination of at least two different statistical functions characterising the evaluated input signal on the basis of non-linear signal processing.

A typical modification would be applied for the purpose of obtaining automatic equalisation of loudness, although other types of gain control may be applied within the scope of the invention.

According to the invention, a non-linearity may form a necessary and advantageous way of deriving a representative loudness estimate.

In an embodiment of the invention said at least one non-linear function (NLF) is established by an artificial neural network (ANN: artificial neural network).

In an embodiment of the invention said artificial neural network comprises a multilayer perceptron.

In an embodiment of the invention said at least one non-linear function is established by means of polynomial fitting.

In an embodiment of the invention said at least one non-linear function is established by means of splining.

In an embodiment of the invention the evaluation is established by a serial, a parallel or a combination thereof of at least two non-linear functions (NLF).

According to the invention, an overall desired evaluation may advantageously be split up in several different non-linear signal processing steps. Examples of such splitting may, e.g., comprise a pre-processing of an input signal performed by at least one non-linear function in one or several bands or partial representations of the input signal prior to a non-linear processing of the individual or combined representations obtained by the pre-processing. An example of such pre-processing may, e.g., be establishment of non-linear typically well-known statistical functions representing the input signal in one or several bands according to predetermined signal processing and subsequently performing a signal processing of the combined signals on the basis of one or several non-linear functions. The subsequent one or several non-linear functions will typically be non-linear functions adapted specifically for the purpose of bringing the result of the established pre-filtering into an estimate of perception intensity.

Evidently, further processing steps than the above-described may be inserted prior to, between and after the above-explained processing steps.

In an embodiment of the invention said perception intensity comprises loudness.

In an embodiment of the invention said perception intensity comprises sharpness, annoyance, airiness, punchiness, brilliance, presence, fatness, deepness and edginess or any combination thereof.

In an embodiment of the invention the estimation of said time variant distribution function (TVDF) is made on the basis of at least two different feature characterizing parameters of said audio input signal (IS)

In an embodiment of the invention at least one of said at least two different characterizing functions comprises a time variant statistical function.

According to a preferred embodiment of the invention, two statistical functions are applied as a combined representation of the desired time variant distribution function.

In an embodiment of the invention at least one of said feature characterizing parameters comprises a central value over time, such as a mean value, an average value and/or a median.

In an embodiment of the invention at least one of said feature characterizing parameters comprises a measure of the spread over time, standard deviation, variance or inter quartile range.

In an embodiment of the invention preprocessing of the audio input signal is done prior to the establishment of said at least two feature characterizing parameters.

In an embodiment of the invention said time variant distribution function is determined in a time window.

According to an advantageous embodiment of the invention, the time variant distribution function should be determined as a function of time and in a time window of the input signal. In this way, a runtime updating of the perception intensity may be obtained and, moreover, when applying a time window, a memory in the method with respect to previous behavior of the input signal.

Examples of a runtime window would range from, e.g., approximately 1/10 second and, e.g., up to 30 seconds. Evidently, the window may in principle be much larger than 30 seconds, solely depending on the input signal to be evaluated and the intentions of the user. An overall evaluation of perception intensity of an audio signal, e.g. an audio track of a CD or several minutes, may, thus, be evaluated according to the invention if so desired.

In an embodiment of the invention at least two different partial representations (PR1, PR2, . . . PRn) of the audio input signal (IS) are established, at least two different statistical functions (SF1, SF2, SFn) are established on the basis of at least one of said different partial representations (PR1, PR2, . . . PRn) of said audio input signal (IS), said determined statistical functions are combined into a loudness representation by means of at least one non-linear signal processing.

According to a preferred embodiment of the invention, the loudness estimation is initially performed on the basis of an (initial) individual analysis of different bands of the complete audio input signals, which are subsequently combined into at least one, preferably one, combined loudness estimate.

In an embodiment of the invention said audio input signal is modified on the basis of said evaluated perception intensity.

According to the invention the evaluated perception intensity should preferably from the basis of a modification of the input signal or an input signal corresponding thereto. The modification should preferably be automatic by means of signal processing hardware.

In an embodiment of the invention said modifying of the audio input signal is performed as a gain control of the complete or a part of the audio input signal (IS).

According to an embodiment of the invention, different controlling of the input signal may be performed on the basis of the determined loudness estimate although a simple straightforward gain control may typically be quite sufficient in order to establish, e.g., a somewhat smoothed loudness between different input signals. In some embodiments, however, a gain control may, e.g., be narrowed to a certain band or certain bands, e.g. by a boosting or a damping of parts or a part of the input signal.

In an embodiment of the invention said audio input signal (IS) comprises a multichannel signal.

According to an embodiment of the invention, a multichannel signal may, e.g., comprise a stereo signal, a five or six-channel surround sound signal format, etc, all representing an audio representation which may be evaluated advantageously into one or a number of perception intensity representations. One of these may, e.g., be an overall loudness perception intensity of the complete multi-channel signal.

In an embodiment of the invention the perception intensity refers to one shared parameter evaluation of the audio input signal or a derivative thereof.

In an embodiment of the invention the audio input signal or a derivative thereof is evaluated with respect to two or more different types of perception intensity and combinations thereof.

According to an embodiment of the invention, the perception intensity of an audio input signal may comprise sharpness, annoyance, airiness, punchiness brilliance, presence, fatness, deepness and edginess or any combination thereof. In other words, an example of a more complex evaluation of an input signal would be an evaluation of a 5.1 audio input signal with respect to loudness and annoyance.

In an embodiment of the invention said method is implemented in signal processing hardware, such as a digital signal processor and optional supporting electrical circuitry.

In an embodiment of the invention said non-linear function (NLF) is established on the basis of adaptation data (AD).

Adaptation AD could e.g. be registering the user behavior of a signal processing device, e.g. a consumer amplifier, and modifying the performed signal processing accordingly. A specific example of such embodiment may be an amplifier, which may be used in a "learn-mode" by a user and combined with a registered user behavior—e.g. a registering of the user settings, modifying the function of the block ASP. This embodiment is in particular advantageous when applying a non-linear transfer function established by a neural network, as the learn mode may be activated on a run-time basis if so desired.

Adaptation data AD could also be a previously collected data set.

Moreover, the invention relates to a perception intensity estimating device comprising signal processing means performing the method according to any of the claims 1-34.

In an embodiment of the invention, the device comprises monitoring means for displaying the estimated perception intensity.

In an embodiment of the invention, the device comprises control means for controlling connected electronic circuitry in response to the established perception intensity.

Moreover, the invention relates to the use of perception intensity established according to any of the claims 1-34 for automatic control of electronic circuitry.

THE DRAWINGS

The invention will now be described with reference to the drawings of which

FIG. 1 illustrates an exemplary audio signal to be evaluated according to an embodiment of the invention, FIG. 2 illustrates specific applicable distribution function characterizing features, FIG. 3 illustrates the distribution of amplitude of the first two second segment of FIG. 1, FIG. 4 illustrates the distribution of amplitude of the second two second segment of FIG. 1, FIG. 5 illustrates the distribution of amplitude of the third two second segment of FIG. 1, FIG. 6 illustrates the distribution of amplitude of the fourth two second segment of FIG. 1, FIG. 7 illustrates the distribution of amplitude of the fifth two second segment of FIG. 1, FIG. 8 illustrates the distribution of amplitude of the sixth two second segment of FIG. 1, FIG. 9 illustrates the extracted feature parameters of FIG. 1 as a function of time, FIG. 10 illustrates the resultant obtained loudness estimates related to the audio signal of FIG. 1, FIGS. 11-13 illustrate a further embodiment of the invention applying a multiband evaluation of the input signal of FIG. 1, FIG. 14 illustrates a more general evaluation principle of the invention, FIGS. 15A and 15B illustrate two examples of evaluation principles of the invention, FIG. 16 illustrates a more general control principle of the invention, FIG. 17 illustrates a flow chart of an applicable evaluation and control algorithm according to an embodiment of the invention, FIGS. 18A-18D illustrate different examples of distribution function characterizing parameters, and FIG. 19 illustrates a hardware implemented preferred device according to an embodiment of the invention.

DETAILED DESCRIPTION

Initially, an embodiment of the invention will be described specifically with reference to a specific time varying audio sequence and related to loudness evaluation.

A more detailed and general explanation of the invention will be given subsequently.

FIG. 1 illustrates a time domain amplitude representation of a twelve second audio signal as a function of time.

Basically, the illustrated audio signal was constructed to represent six different audio signals each forming a two second sound segment window from each of the following sound segments: a A) 1 kHz tone, B) Pink noise C) Reference female speech D) Rock music E) Big band jazz F) Clarinet duet According to the invention an audio input signal, preferably in the forms of one or a number of sample streams, should initially be processed in order to extract the necessary and sufficient input signal characterizing features. Examples of such time variant characterizing features are inter quartile range, median, sum of squares, percentiles, average, maximum, minimum, standard deviation, sum or variance and combinations thereof. The combination of these characterizing features should, according to the invention, characterize the distribution function of the audio input signals. The necessary exactness of the time varying functions may vary depending on the desired type of evaluation and the type of input signal. It is generally desired that a two-dimensional representation of the time varying distributing function representing the input signal is obtained.

FIG. 2 illustrates the principles of some specific time variant distribution function characterizing features applied according to a specific embodiment of the invention. It is noted that several other time variant features may, of course, be applied for the purpose.

The specifically chosen and illustrated parameters are statistical parameters such as maximum, median and inter quartile range (IQR), defined as the distance between the first and third quartile of a specific statistical representation of an input audio signal. The illustrated characterizing features are well-known within the art.

In the following, each of the abovementioned six two-second segments will be analyzed individually and non-overlapping in a single frequency band. The two calculated signal features are: the median and the inter-quartile range (IQR) of the dB magnitude of the signal. These two functions are commonly used in descriptive statistics as robust measurements of the central tendency and the spread of a distribution, respectively.

Figure 9:
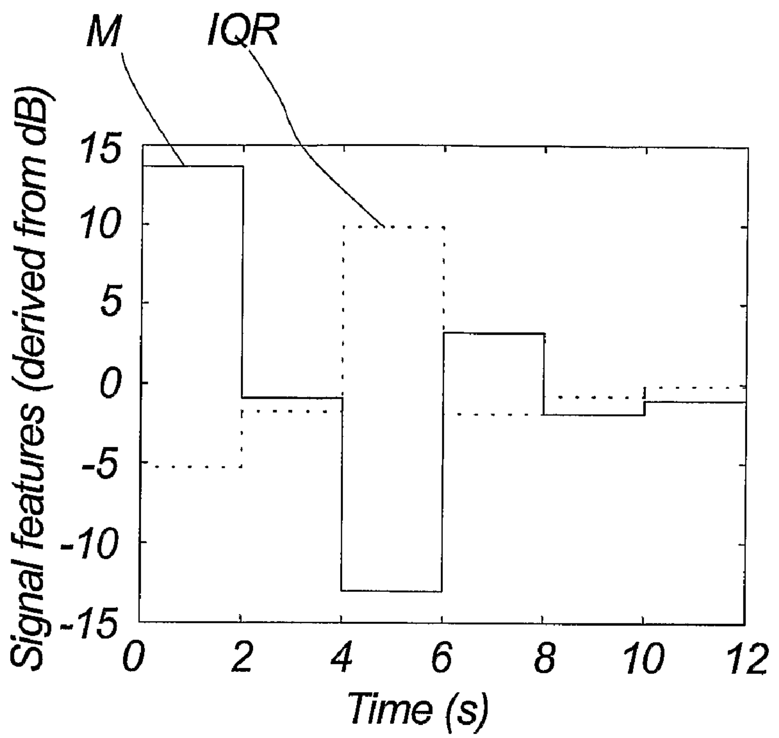

In FIG. 9, the extracted inter quartile range IQR and the median M are illustrated as a function of time. Each of the initially described sound segments are, thus, now described by a two-dimensional description of the distribution function, namely by a median and an IQR of each sound segment.

Figure 10:
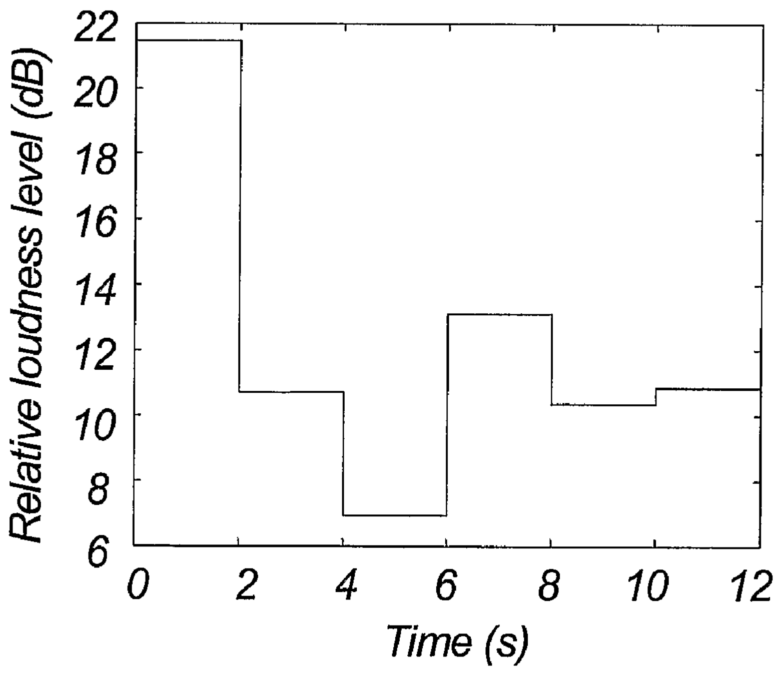

In FIG. 10 the two-dimensional description of the distribution function has been combined into one loudness estimate related to each clip by means of non-linear function. The non-linear function may, e.g., be provided by an artificial neural network trained by data representing different tests performed by test persons.

Figure 11:
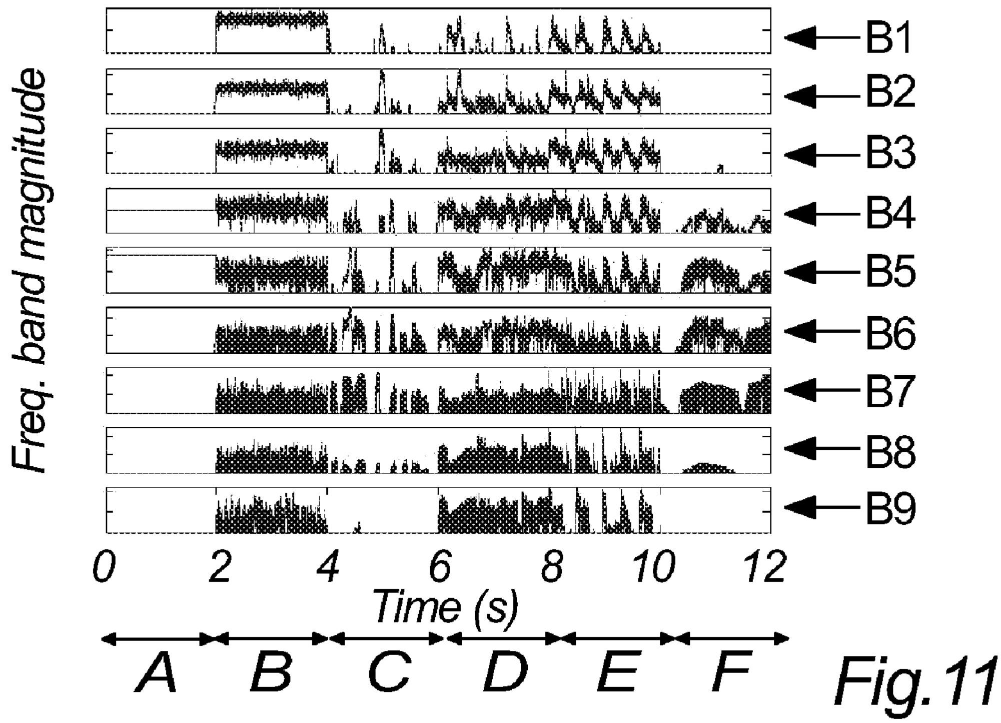

Turning now to FIG. 11 an alternative and preferred embodiment of the invention will be described.

According to the illustrated embodiment of an evaluation of perception intensity—in this embodiment loudness—the input audio signal is initially divided into nine octave bands B1 to B9. The magnitude in each octave frequency band B1 to B9 is illustrated in FIG. 11 as a function of time. Still, the evaluated input signal corresponds to the already described twelve second signal of FIG. 1.

Figure 12:
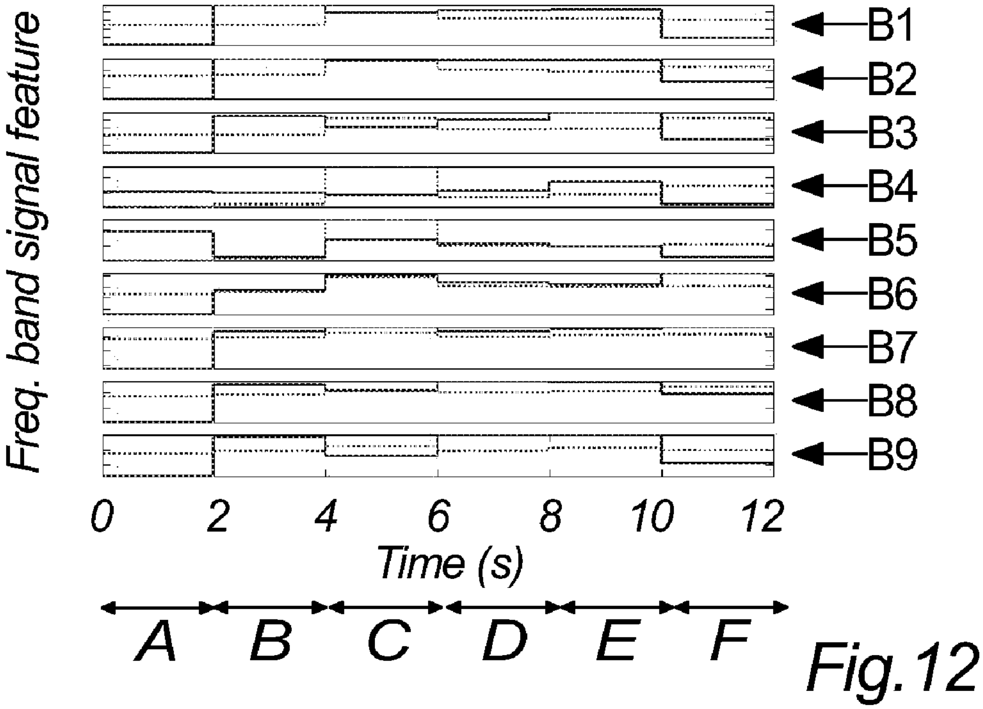

In FIG. 12 the basic establishment of a distribution function described by two parameters, inter quartile range IQR and median M as explained with reference to the FIGS. 3-9 is repeated and illustrated for each octave band B1 to B9.

Figure 13:
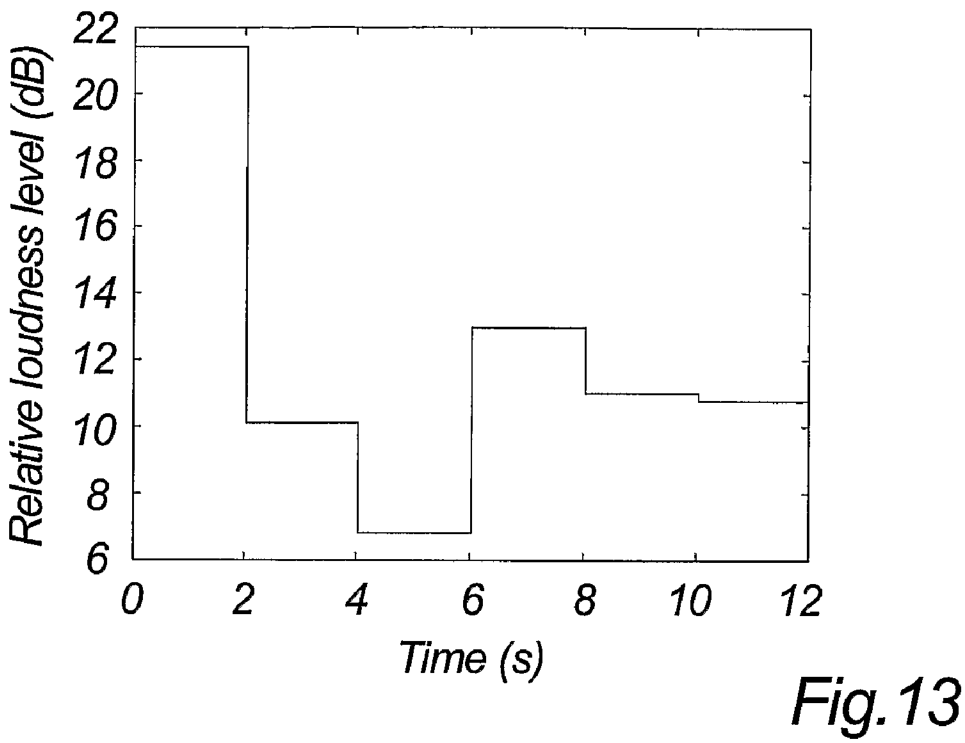

In FIG. 13 the nine distribution functions of FIG. 12, each represented by inter quartile range IQR and median M, have been processed into one resulting loudness estimate of each sound segment A to F by means of a non-linear function. It is noted that the resulting loudness estimation essentially corresponds to the loudness estimation obtained by one-band analysis. In this context it should, however, be noted that a multiband approach is preferred.

Figure 14:
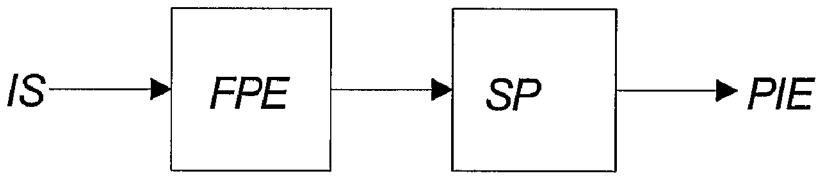

FIG. 14 illustrates a more general evaluation principle of the invention,

An audio input signal representation IS is input to a block FPE performing feature parameter extraction. The performing feature parameter extraction has the purpose of representing the input signal IS suitably for the further evaluation of the signal.

The audio representative input signal must be represented in a certain way to facilitate the desired evaluation of perception intensity. Basically an at least two-dimensional statistical description over time of the input signal must be estimated for the purpose of evaluating perception intensity according to the invention. More specifically such a two-dimensional description of the input signal is referred to as a distribution function of the input signal.

Several different statistical functions may be applied within the scope of the invention. Examples of such function may be inter quartile range, median, sum of squares, percentiles, average, maximum, minimum, standard deviation, sum, variance.

It must be stressed that the description of the shape of the distribution function may be obtained in several different ways, e.g. by means of at least two at least partly linear independent functions. Evidently, further descriptive parameters, i.e. further dimensional description serving the purpose of providing a more detailed description of the distribution function, may be applied according to the invention. It should also be noted that a partial description of the distribution function of the input signal according to the invention may also be obtained by more conventional filtering typically not associated as a statistical function. An example of such is a mean value over a time interval which may be e.g. be obtained by a conventional integrating filter.

It should, moreover, be noted that the shape of a distribution function preferably refers to a shape of a function which has been fixed with respect to the axis of the distribution function.

In this context it should, generally, be stressed that various processing may occur both prior to and subsequently to the estimation of a distribution function of an input audio signal within the scope of the invention. Examples of such pre or post processing is the use of an asymmetrical low pass filter, rectification, squaring, evaluation of power functions, taking the logarithm, etc.

Another example is an initial band-pass filtering of an input audio signal into two or several bands for the purpose of individual handling of the different bands prior to the estimation of perception intensity. Such initial splitting of the input signal into different bands may, e.g., ease the process of establishing a non-linear function fitting a relevant perception intensity reference database.

Generally, such preprocessing is preferred, for the purpose of reducing the complexity of the subsequent establishment of a perception intensity estimate.

Specific examples of feature parameters of an input signal have already been given in FIGS. 3 to 8.

The length of the time intervals of the input signal applied for extraction of feature parameters may vary from application to application. Likewise, the interval between the evaluation of a new perception intensity estimate may vary. The two mentioned intervals do not necessarily need to be identical.

In the next block SP a signal processing is performed and a resulting perception intensity estimate PIE is output.

It is stressed that the invention, although very advantageous with respect to loudness as explained above, may be utilized for evaluation of very different types of perception intensity such as sharpness, annoyance, and airiness. In this context it is noted that the invention features a very advantageous adaptation to each purpose as the invention basically needs to adapt ultimately one non-linear function to the purpose as the rest of the processing equipment and critical settings may be fixed or principally fixed. In this context it is noted that an initial setting of a non-linear function may be changed over time, e.g. on the basis of user behavior.

According to an advantageous and preferred embodiment of the invention the signal processing performed in the block SP is based on a non-linear transfer function.

The preferred processing of the estimated distribution function is non-linear as the available non-linear processing is very advantageous in connection with complex evaluation of two or several input parameters. One reason is that a non-linear function may be established on the basis of a multidimensional input by machine-learning, e.g. by means of a neural network.

Several different non-linear functions may, generally, be applied according to the invention. Examples of such functions will be given below.

Although the non-linear function has proven to be very advantageous for the purpose of evaluating perception intensity, it has proved to be a particular strong evaluation basis when evaluating audio signals represented by distribution function descriptive parameters. Preferred descriptive parameters comprise two substantially orthogonal or linearly independent descriptive parameters expressing a central tendency and a spread of distribution of preferably the amplitude of an input signal.

The resulting perception intensity estimate PIE may, e.g., be fed to a perception intensity metering for a run-time monitoring of the perception intensity of the input signal IS. En example of such meter may be a loudness meter.

Evidently, several other blocks or steps may be added to the illustrated embodiment between the processing blocks and as pre-processing, post-processing or combinations thereof. An example of such embodiment will be described subsequently with reference to FIG. 17. Preprocessing would, e.g., serve the purpose of reducing complexity of the audio input signal and, thereby, facilitate a more efficient establishment of a distribution function.

Figure 15A:
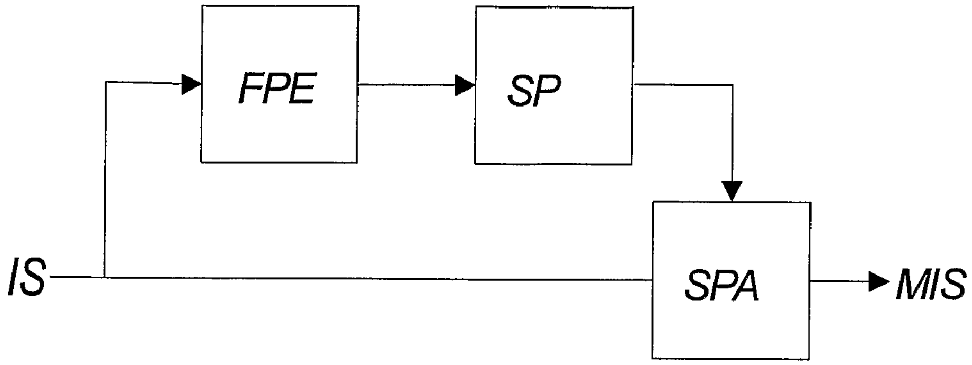

FIG. 15A illustrates an example of a general control principle of the invention based on the embodiment illustrated in the above FIG. 14.

In this embodiment an input signal IS is feature extracted in a feature extraction block FPE and perception intensity estimate is subsequently established on the basis of the distribution function established by block FPE.

Moreover, the input signal IS is bypassed to a signal processing block SPA and the input signal IS may then be processed according to the perception intensity estimate PIE established by the block SP. The resulting modified audio signal MIS is subsequently output. A real-life example of such an embodiment is an automatic gain control of an input signal IS.

Figure 15B:
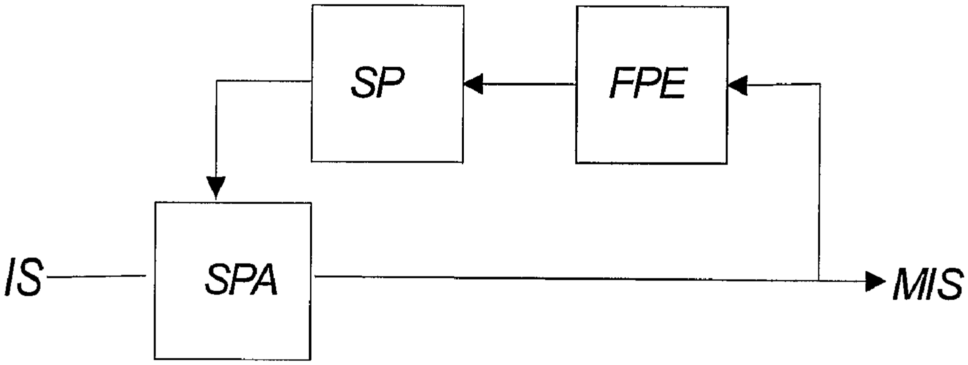

FIG. 15B illustrates a further example of a control principle of the invention based on the embodiment illustrated in the above FIG. 14; basically a variant of FIG. 15A.

An input signal IS is fed to a signal processing block SPA and the input signal IS may then be processed according to the perception intensity estimate PIE established by the block SP. The resulting modified audio signal MIS is subsequently output. A real-life example of such an embodiment is an automatic gain control of an input signal IS. According to this embodiment, however, the feature extraction is performed on the resulting modified output signal.

Figure 16:
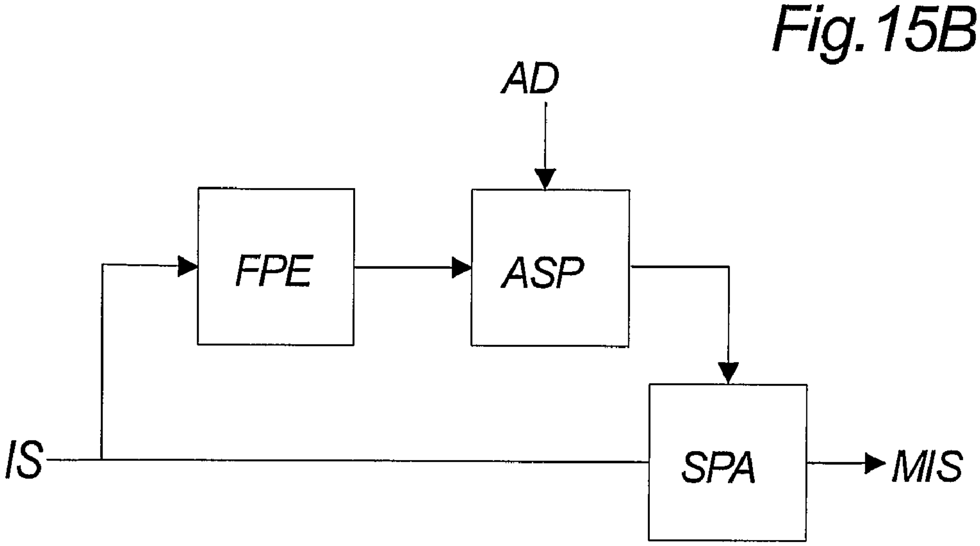

FIG. 16 illustrates a further embodiment of the invention basically corresponding to the above-illustrated embodiment but now the signal processing block SP of FIG. 15A or 15B has been exchanged with an adaptive signal processing block ASP.

The adaptive signal processing block is adapted for adaptation data AD. Adaptation AD could e.g. be registering the user behavior of a signal processing device, e.g. a consumer amplifier, and modifying the performed signal processing accordingly. A specific example of such embodiment may be an amplifier, which may be used in a "learn-mode" by a user and combined with a registered user behavior—e.g. a registering of the user settings, modifying the function of the block ASP. This embodiment is in particular advantageous when applying a non-linear transfer function established by a neural network, as the learn mode may be activated on a run-time basis if so desired.

Adaptation data AD could also be a previously collected data set.

Figure 17:
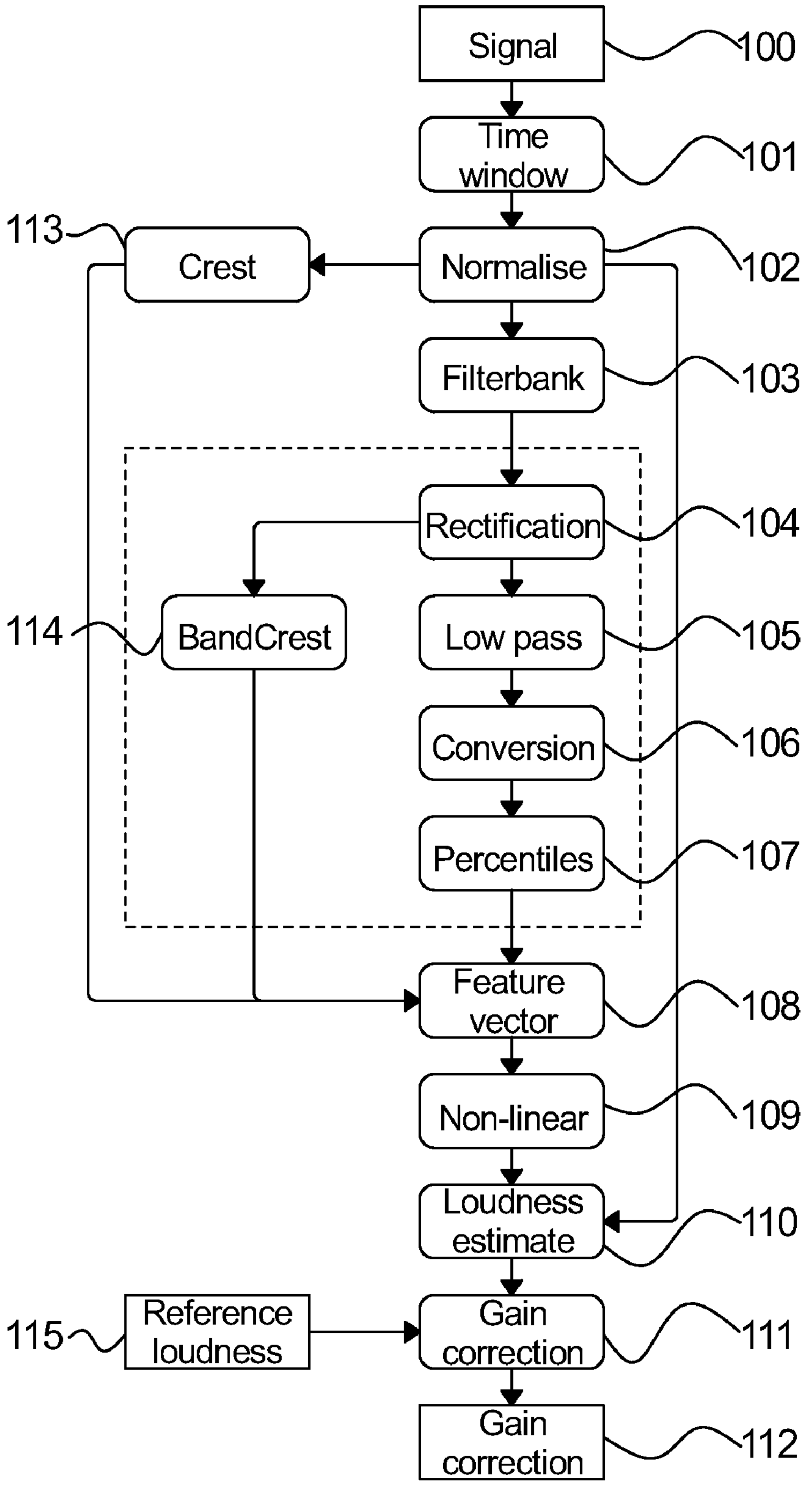

FIG. 17 illustrates a flow chart of an applicable evaluation and control algorithm according to an embodiment of the invention.

Figure 1:
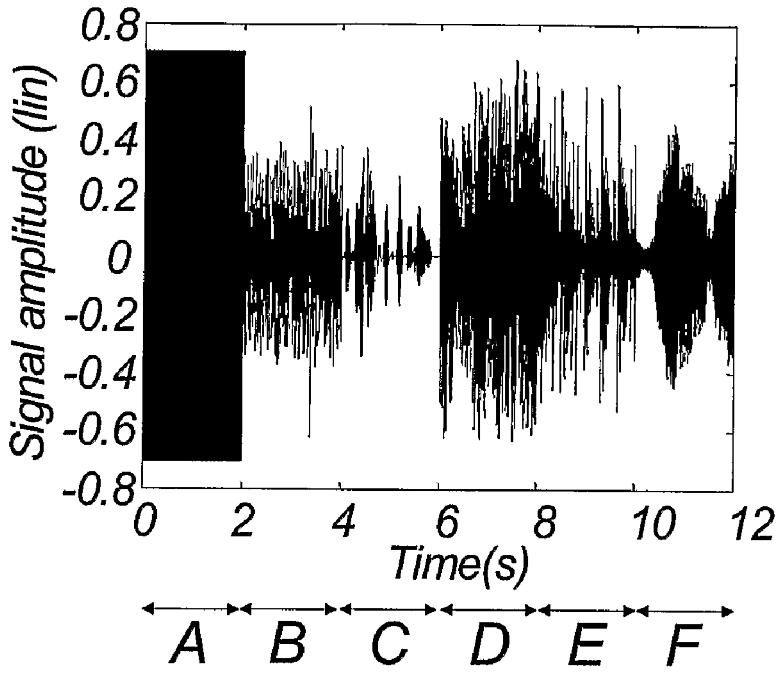
Figure 2:
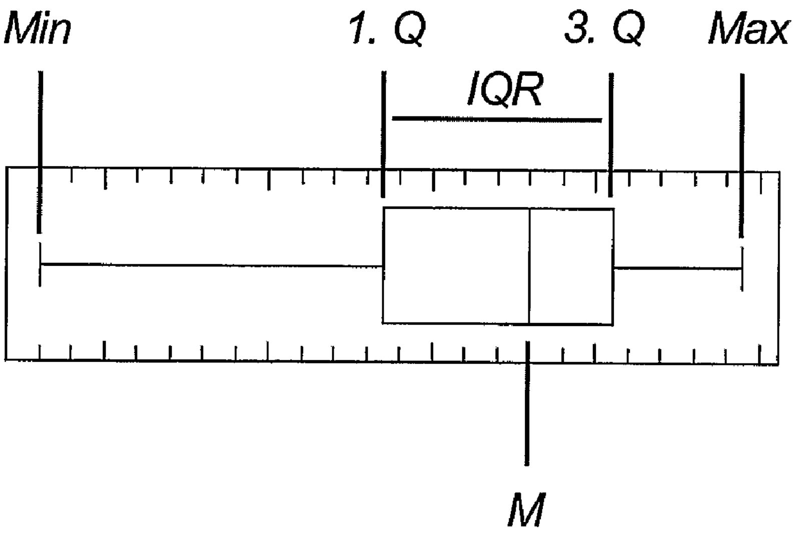
Figure 3:
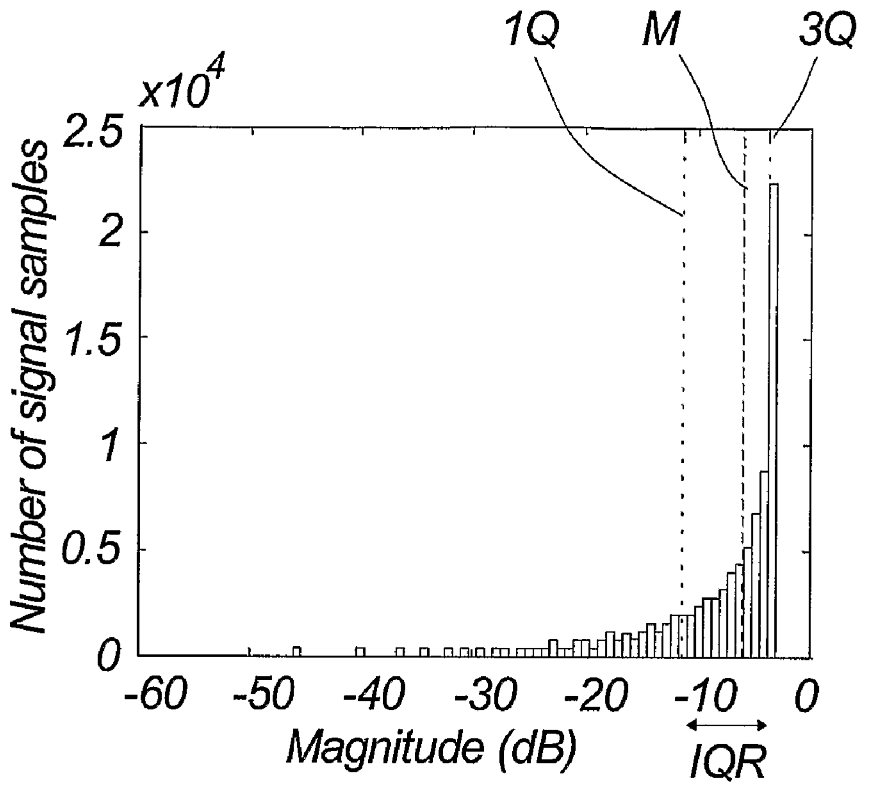
FIG. 3 illustrates the distribution of amplitude of the first two second segment A, namely the lkHz tone. The $1^{st}$ quartile, $3^{rd}$ quartile and the median are marked up as 1Q, 3Q and M, respectively.
Figure 4:
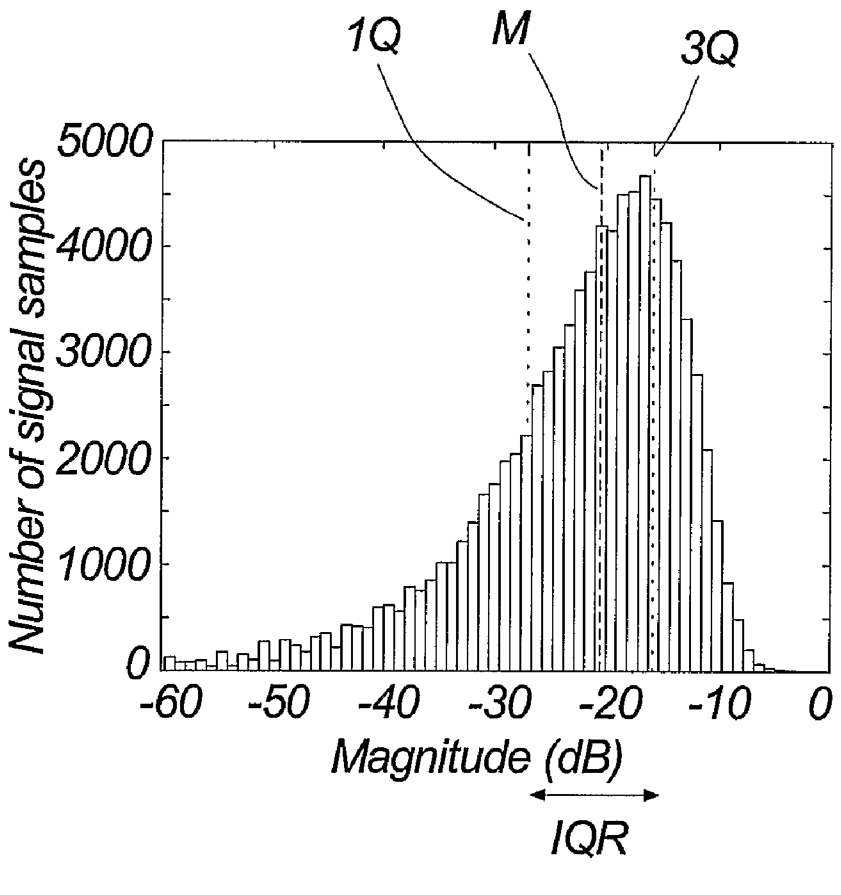
FIG. 4 illustrates the distribution of amplitude of the second two second segment B, namely the pink noise. The $1^{st}$ quartile, $3^{rd}$ quartile and the median are marked up as 1Q, 3Q and M, respectively.
Figure 5:
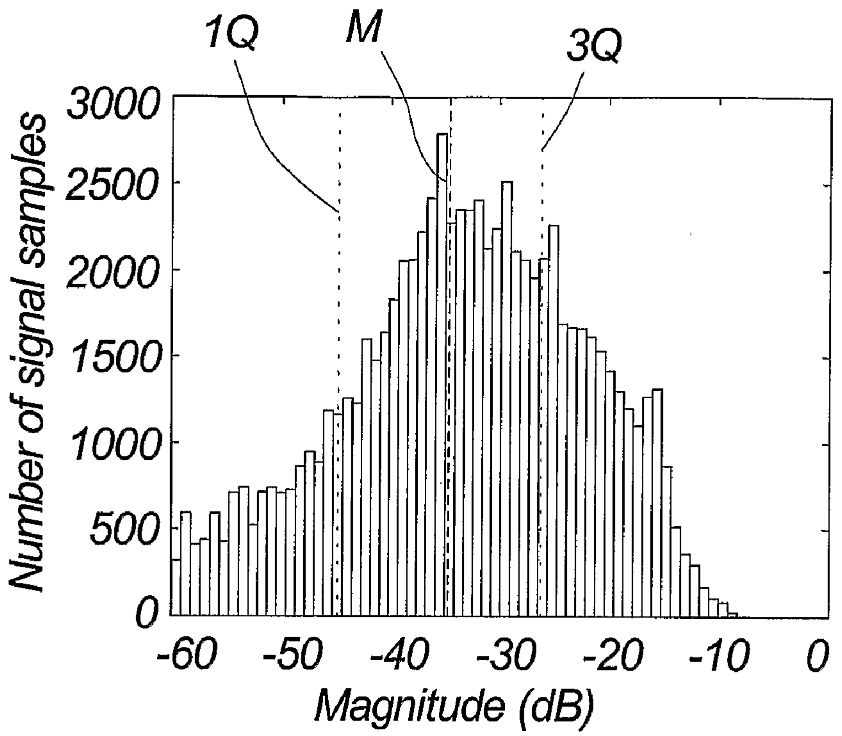
FIG. 5 illustrates the distribution of amplitude of the third two second segment C, namely the speech signal. The $1^{st}$ quartile, $3^{rd}$ quartile and the median are marked up as 1Q, 3Q and M, respectively.
Figure 6:
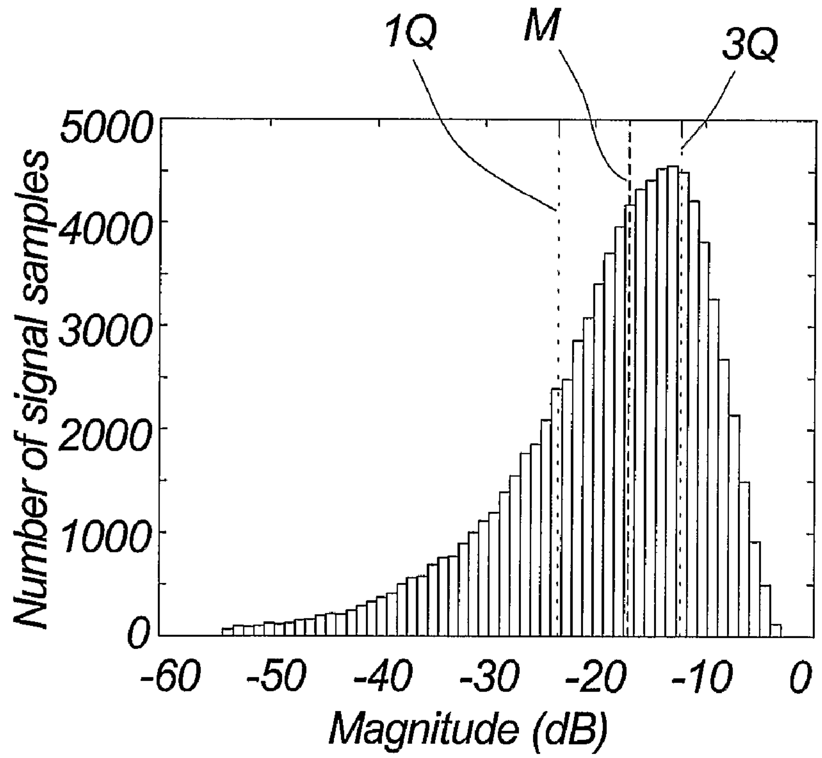
FIG. 6 illustrates the distribution of amplitude of the fourth two second segment D, namely the rock music signal. The $1^{st}$ quartile, $3^{rd}$ quartile and the median are marked up as 1Q, 3Q and M, respectively.
Figure 7:
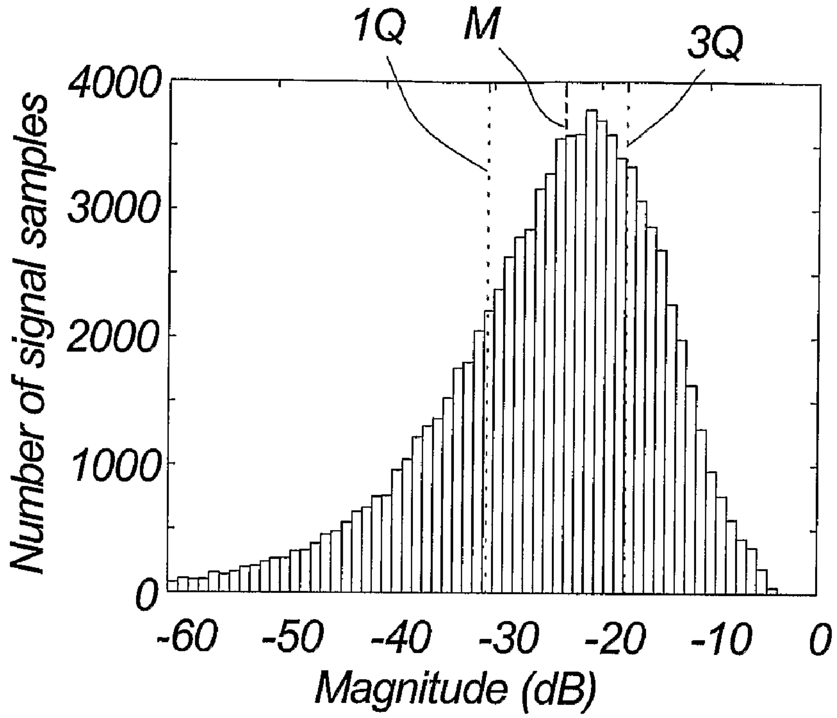
FIG. 7 illustrates the distribution of amplitude of the fifth two second segment E namely the big band signal. The $1^{st}$ quartile, $3^{rd}$ quartile and the median are marked up as 1Q, 3Q and M, respectively.
Figure 8:
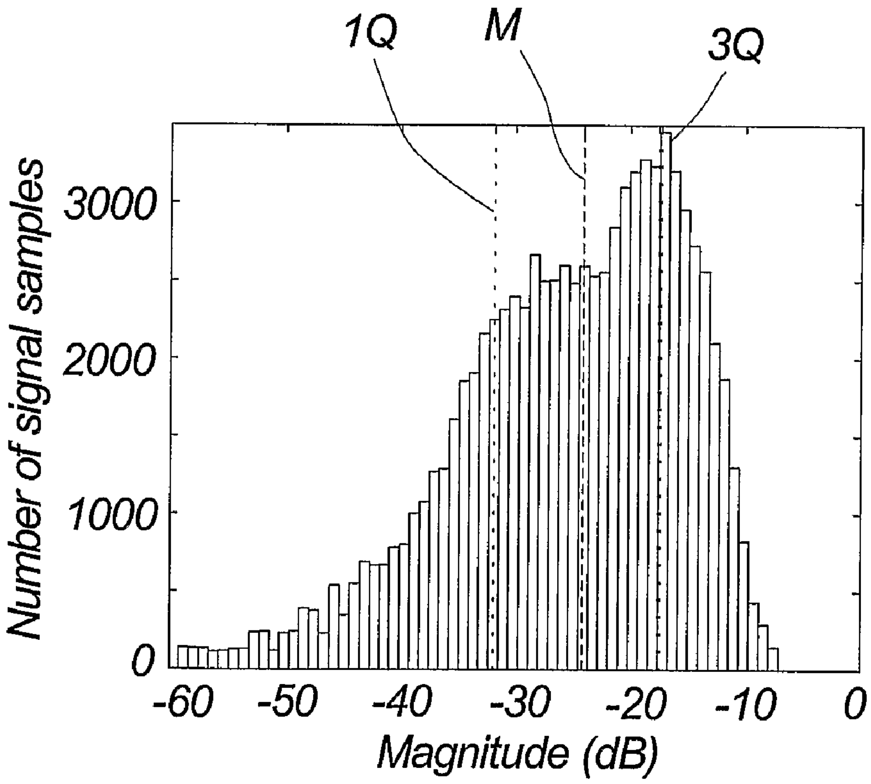
FIG. 8 illustrates the distribution of amplitude of the sixth two second segment F, namely the clarinet duo signal. The $1^{st}$ quartile, $3^{rd}$ quartile and the median are marked up as 1Q, 3Q and M, respectively.

The described flow chart may, e.g., be implemented in a signal processing device or signal processing circuitry described in principles according to FIG. 19 and applied on the signals described with reference to FIG. 1.

Initially, in step 100 an audio signal representation is provided, typically in the form of a digital audio signal. Evidently, an analog program material may be applied although an initial A/D conversion would be strongly preferred for the purpose of a subsequent streamlined and efficient signal processing.

In step 101 a time window is applied to the provided audio signal representation. In the illustrated embodiment, the selected window is chosen to be the individual sound segments; that is, the six different audio signals as explained with reference to FIG. 1. The use of such discrete non-overlapping sound segments is here applied, as only a single number representing the relative loudness of each segment is desired. Evidently, other approaches to a sliding window may include a complete audio track or, e.g., a true sliding window comprising a dynamically sliding audio window having a certain, typically fixed, time length. The time length may, e.g., be a 1.5 second window.

In step 102 the input audio signal is normalised in level in order to optimize use of the dynamic range of the following steps. The normalization is performed by using a weighted RMS measurement. This level normalisation is compensated at the end of the measurement procedure.

In step 113 a broadband crest parameter is calculated as the ratio between the overall unweighted RMS value and a pseudo peak value (attack time 1 ms). This value, Crest, is converted into dB.

In step 103 a filterbank is applied as a rough approximation of the frequency analysis in the human ear. The applied filters are octave wide, and an overall bandwidth limitation is also applied.

In step 104 a full wave rectification is applied to the processed signal. Thus, the output of each band is passed through an abs( ) function. This implies that the loudness measurement method is insensitive to the absolute phase of the input signal.

In step 114, for each band, the BandCrest is the maximum value divided by the overall RMS value per band. This value is converted into dB. The BandCrest vector contains one value for each frequency band.

In step 105, each of the rectified filter output signals are filtered with a first order low pass filter with asymmetric time constants to extract the short-term envelope of each band. For rising level the time constant—natural logarithm based—is 20 ms, for falling level the time constant is 50 ms In step 106 the level of the processed signal is converted to level in dB by taking 20 times the logarithm (base 10) of the envelope.

In step 107, for each band, two percentiles are calculated: The 50th percentile (corresponding to the median) and the 90th percentile (corresponding to the value which 10% of the values are above). These two latter statistics are referred to as the lower and the upper percentiles, respectively In step 108 a feature vector is constructed from the following parameters:

- The full set of upper percentiles, here 9 values in the feature set.
- The set of upper percentile values minus the lower percentile values (bandwise) called the percentile-difference. Two linear combinations of the percentile-difference values are used, i.e. 2 values.
- Based on the Crest and the BandCrest values. Two linear combinations of the Crest parameters are used, i.e. 2 values.

Each of the linear combinations is implemented by first subtracting a constant value from each contributing parameter, and then multiplying the result by another constant value.

Finally, the products are summed:

$$lincom = \sum_{i=1}^{N} (parameter_i - b_i) \cdot w_i$$

N is the number of parameters in each vector. For the percentile differences N=9. For the crest parameters, N=10.

In step 109 the non-linear function is established for the purpose of mapping the feature parameters into a loudness estimate.

To estimate the loudness value based on the feature set an artificial neural network is employed. The applied network comprises a multi-layer perceptron type having a tan-sigmoid activation function for the units in the single hidden layer and, moreover, it comprises a single output unit with a linear activation function. The tan-sigmoid activation function is expressed as:

$$f(x) = 1 - \frac{2}{1 + e^{2x}} = \tanh(x)$$

The topology of the neural network is as follows: There are thirteen input units (normalised features). The first nine represent bands 1-9 from the reference signal, the last 2 plus 2 are the percentile difference and crest features, respectively. These thirteen input units are connected to hidden-layer units of the ANN, and the hidden-layer units are in turn connected to the single output unit. The input to the neural network, thus, consists of the 9+2+2 feature parameters, normalised by addition of real-valued constants in the range [−50,50], and multiplication by real-valued constants in the range [0,10]. The weights connecting the units of the network are optimised to predict the perceived loudness. The neural network weights are real-valued constants in the range [−16,16], and the bias values are real-valued constants in the range [−3,71].

In step 110 a loudness estimate is determined on the basis of the above-described non-linear function provided according to the previous step.

The last step in computing the relative loudness level value consists of de-normalising the output of the neural network. This may be done by adding the weighted level measured at the start in step 102 to the output of the neural network.

In step 115 the loudness of a reference signal is provided.

Using the model as described in the previous, the loudness of a reference signal is estimated corresponding to the output of block 110. This value is kept as a constant within the model in order to enable calculation of gain correction values. The model itself does not assume any particular relationship between digital levels and playback SPL but a practical value for some purposes would be 100 dB SPL for digital full scale. With this assumption the loudness level estimate of a specific reference signal used is: 72.2 dB (phon).

In step 111 and 112, a gain correction is computed.

This is done by subtracting the measured loudness estimate from the stored reference loudness. This results in the desired relative loudness estimate expressed as the gain correction having to bring the tested sound segment to the same perceived level as the reference segment. Evidently, such estimate may freely be established or calculated according to other methods or ideas of presentation.

Note that certain steps of the above-described flowchart may be omitted and that the flow chart may include several further process steps within the scope of the invention.

FIG. 18A to FIG. 18D illustrate different combinations of distribution characterizing parameters applicable within the scope of the invention. The estimation characterizing parameters, i.e. shape defining parameters, are applied to the same distribution function TVDF. The distribution function TVDF is mapped in as numbers of signal samples per time unit NSS as a function of amplitude A of an audio input signal.

Figure 18A:
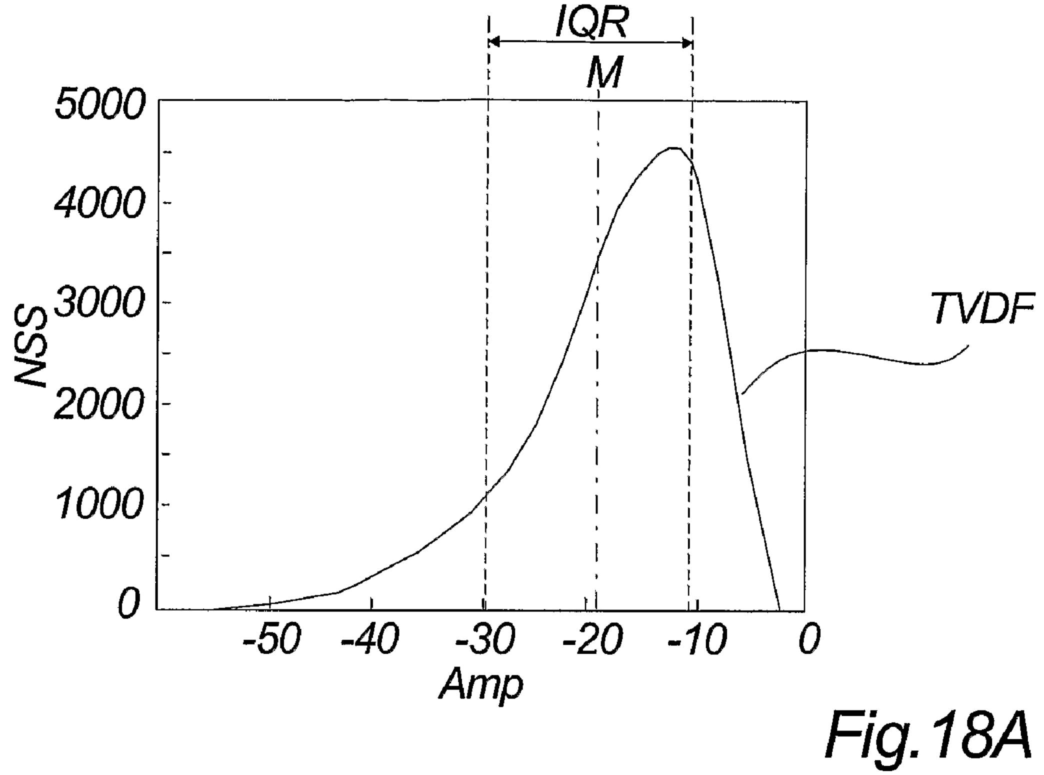

In FIG. 18A the distribution function TVDF of an input signal is characterized by two shape-defining parameters, namely interquartile range IQR and median M.

Figure 18B:
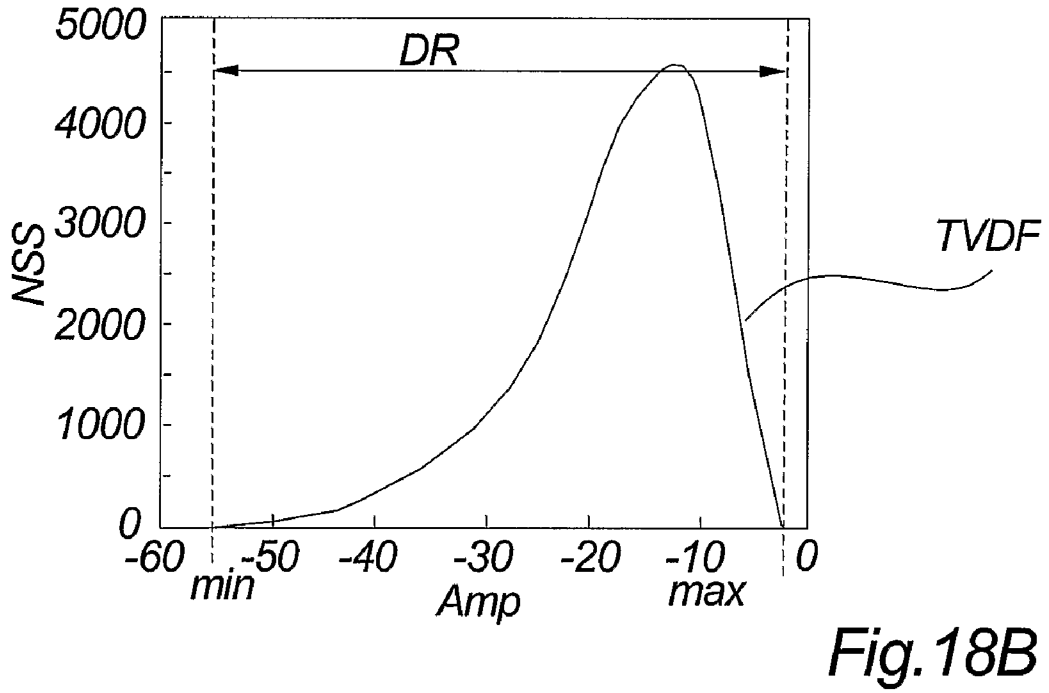

In FIG. 18B the distribution function of an input signal is characterized by three shape defining parameters, namely distribution range DR, a minimum amplitude value MIN, and a maximum amplitude value MAX. Evidently, the shape of distribution may, basically, be said to be represented completely by two distribution characterizing parameters, namely the distribution range DR and one of the amplitude values MIN or MAX.

Figure 18C:
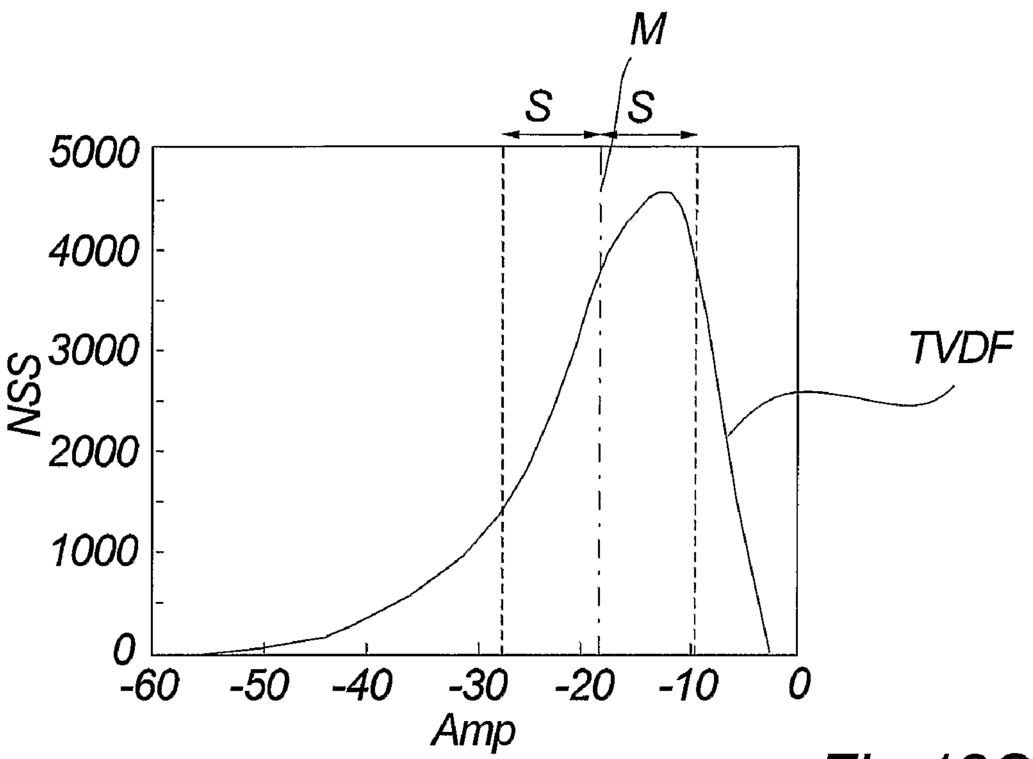

In FIG. 18C the distribution function of an input signal is characterized by the mean value M and the standard deviation S.

Several others than the above-listed distribution function characterizing parameters may be applied according to the invention. Examples of such parameters are listed below. Moreover, it should be noted that the distribution function may be estimated by more than two characterizing parameters, e.g. four, namely a combination of the illustrated parameters of FIGS. 18A and 18B, i.e. median, interquartile range, max value and distribution range.

Figure 18D:
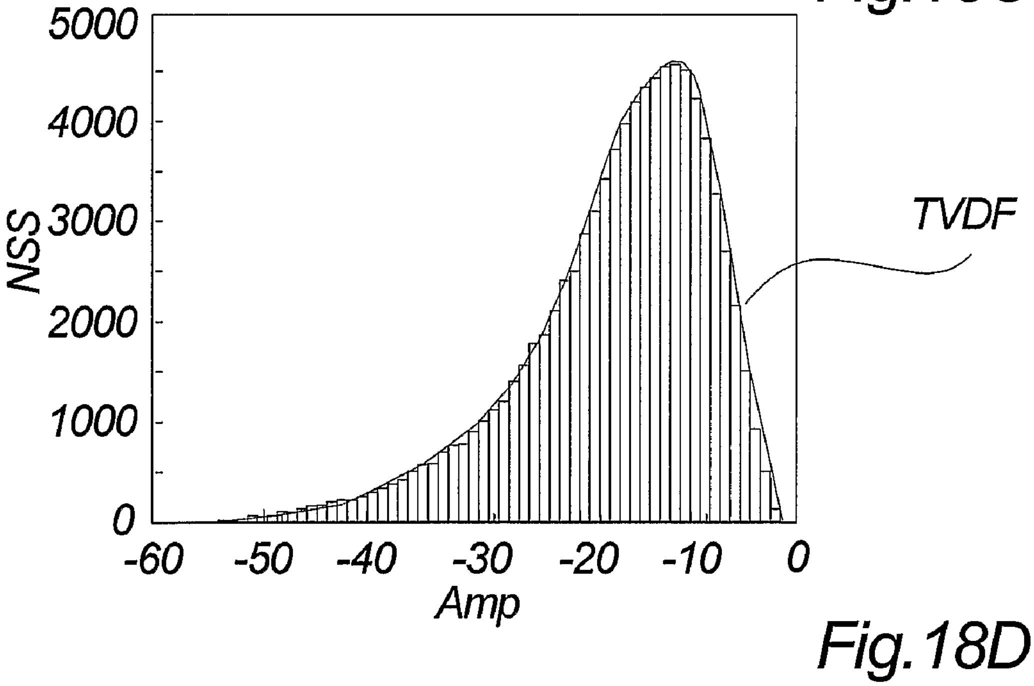

In FIG. 18D the distribution function of an input signal is represented by a histogram. Evidently, such an estimation of the distribution may be regarded as a brute-force estimation of the distribution function where the requirements with respect to signal processing depends on the resolution of the amplitude, i.e. the number of bins.

Applicable distribution function characterizing parameters.

Below is a list of various common scalar or 1-dimensional statistical parameters that may characterize the distribution of a given data sample. For instance, the location, the spread, or the symmetry of the distribution may be measured. In each case, the parameter is calculated from a set of n sample values, denoted $x_i$ (i=1 . . . n).

Mean Values:

The arithmetic mean, $$\bar{x} = \frac{1}{n}\sum x_i$$

The geometric mean, $$GeoMean = \sqrt[n]{\prod x_i}$$

The harmonic mean, $$HarmMean = n \Big/ \sum \frac{1}{x_i}$$

Variance, and Standard Deviation:

The sample variance, $$\mathrm{Var} = \frac{1}{n-1}\sum (x_i - \bar{x})^2$$

The standard deviation, $$s = \sqrt{\frac{1}{n-1}\sum (x_i - \bar{x})^2} = \sqrt{\mathrm{Var}(x)}$$

Average Absolute Deviation and Median Absolute Deviation

The average absolute deviation (AAD) is defined as, $$AAD = \frac{1}{n}\sum |x_i - \bar{x}|$$

The median absolute deviation (MAD) is defined as, $$\mathrm{MAD} = \mathrm{median}(|x_i - \tilde{x}|)$$

where $\tilde{x}$ is the median of the data x.

Coefficient of Variation:

$$CV = s/\bar{x} * 100\%$$

Min, Max, Range and Mid Range:

The min and max are the minimum and maximum values, respectively.

The range of x is then, $$\mathrm{Range} = \max - \min$$

The mid range is, $$\mathrm{MidRange} = (\min + \max)/2$$

Percentile:

The $r^{th}$ percentile of x is the value such that r percent of the data in x falls at or below that value.

Interpolated Percentile:

Interpolation, such as linear interpolation, may be used in the calculation of the percentile, which makes the percentile parameter 'smoother', in particular in cases with small sample sizes.

Median and Quartiles:

The median is the value such that half of the data in x falls below that value and half above, $$\mathrm{median} = \tilde{x}$$

The first, second and third quartiles are, $Q_1$=the median of the data that falls below the median; this is also the $25^{th}$ percentile.

$Q_2$=the median or the $50^{th}$ percentile.

$Q_3$=the median of the data that falls above the median; this is also the $75^{th}$ percentile.

Inter Quartile Range and Mid Mean:

The inter-quartile range (IQR) is, $$IQR = Q_3 - Q_1$$

The mid mean is,

MidMean=a mean of the data between the $25^{th}$ and $75^{th}$ percentiles

Trimmed Mean and Winsorized Mean

The trimmed mean is similar to the mid mean except that different percentile values are used. A common choice is to trim 5% of the data in both the lower and upper tails of the distribution, i.e. the trimmed mean is the mean of the data between the $5^{th}$ and $95^{th}$ percentiles.

The winsorized mean is similar to the trimmed mean. However, instead of trimming the extreme data samples, they are set to the lowest (or highest) value. For example, all data below the $5^{th}$ percentile is set equal to the value of the $5^{th}$ percentile, and all data greater than the $95^{th}$ percentile is set equal to the $95^{th}$ percentile.

It should be noted that many of the other parameters can be formulated in 'trimmed' or 'Winsorized' versions too.)

Mode:

Mode=the value of the data sample that occurs with the greatest frequency.

For continuous data distributions, any specific value may not occur more than once. Therefore, the mode may be defined as the midpoint of the histogram-interval with the highest peak.

Skewness:

The skewness measures the amount of asymmetry of the distribution, $$\mathrm{Skewness} = \frac{1}{n-1}\sum\left(\frac{x_i - \bar{x}}{s}\right)^3$$

Kurtosis:

The kurtosis measures the concentration of data around the peak and in the tails versus the concentration in the flanks of the distribution.

$$\mathrm{Kurtosis} = \frac{1}{n-1}\sum\left(\frac{x_i - \bar{x}}{s}\right)^4$$

The r'th Central Moment:

$$CentralMoment = \frac{1}{n-1}\sum (x - \bar{x})^r$$

For example, the second central moment (r=2) is the same as the maximum-likelihood estimate of the variance.

Outlier-Detectors:

A) The proportion of the data samples that is higher than m standard deviations above, or lower than m standard deviations below the mean value:

B) The proportion of the samples that is higher than m times IQR above, or lower than m IQR below the median value.

Miscellaneous:

$$WeightedDeviation = \sqrt[3/2]{\frac{1}{n}\sum (x-\bar{x})^{3/2}}$$

It should be emphasized that the above-mentioned exemplary distribution function characterizing parameters may be supplemented or combined with other suitable weights or relevant filters fulfilling the requirements of obtaining a suitable description of a distribution function for the purpose of obtaining an evaluation of perception intensity.

Figure 19:
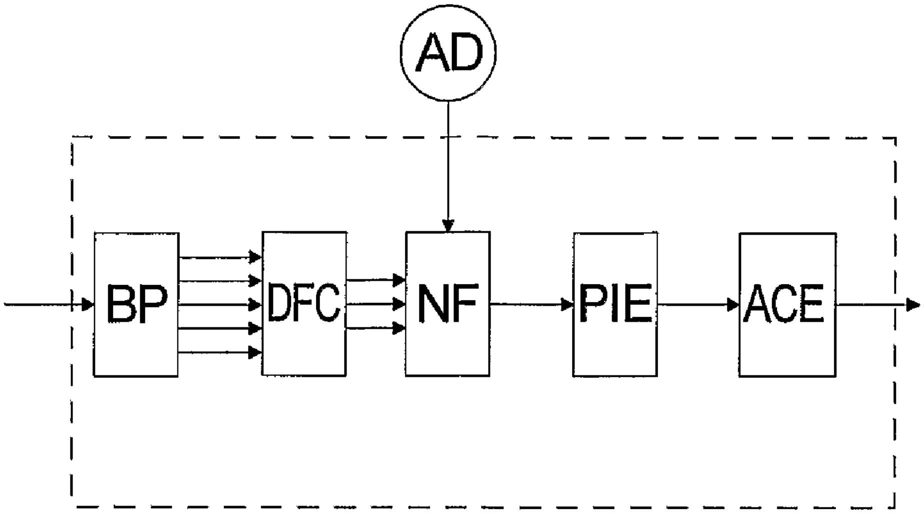

FIG. 19 illustrates a hardware implemented preferred device according to an embodiment of the invention.

The perception intensity evaluator comprises an input block BP comprising a filter bank of band-pass filters, e.g. octave filters adapted in a conventional manner to divide an incoming audio signal into a parallel representation. The parallel representations are fed to an analyzer block DFC. The analyzer block DFC is adapted for extraction of feature parameters of the input signal. Such feature parameters have also been referred to above as distribution function characterizing parameters.

When the distribution function of the individual bands has been established, they are fed to a processing block NF performing a non-linear processing of the parallel signal. The resulting processing is transformed into one expression of the overall perception intensity in the block PIE. Processing block NF may be adapted to adaptation data AD as previously described with reference to FIG. 16.

Subsequently, the established evaluation is fed to a block ACE performing a monitoring of the evaluated perception intensity and/or performing an automatic control of the signal on the basis thereof.

The illustrated hardware may, e.g., be implemented in a Motorola DSP 56303 and optional supporting circuitry.

Moreover, the illustrated device may comprise monitoring means (not shown) for displaying the estimated perception intensity.

Moreover, the illustrated device may comprise control means for controlling connected electronic circuitry in response to the established perception intensity (not shown).

It should finally be stressed that the above examples should in no way be regarded as en exhaustive and full list of every embodiment applicable within the scope of the invention.

The invention claimed is:

1. Method of evaluating perception intensity of an audio input signal comprising:

receiving the audio input signal;

estimating a time variant distribution function on the basis of said audio input signal or a derivative thereof;

determining the perception intensity as at least one perception intensity estimate on the basis of said estimated time variant distribution function;

establishing at least two different partial representations of the audio input signal, establishing at least two different statistical functions on the basis of at least one of said different partial representations of said audio input signal; and combining said determined statistical functions into a perception intensity representation by means of at least one non-linear signal processing.

2. Method of evaluating perception intensity of an audio input signal according to claim 1, wherein said estimating of a time variant distribution function is referring to the audio input signal.

3. Method of evaluating perception intensity of an audio input signal according to claim 1, wherein said estimating of a time variant distribution function is made on the basis of a modified audio input signal.

4. Method of evaluating perception intensity of an audio input signal according to claim 1, wherein said audio input signal comprises a sequence of input samples.

5. Method of evaluating perception intensity of an audio input signal according to claim 1, wherein said perception intensity estimate comprises an output sample.

6. Method of evaluating perception intensity of an audio input signal according to claim 5, wherein the determining of a perception intensity representative output samples is established on the basis of a weighted accumulation of at least two time variant distribution functions estimated at least two different times.

7. Method of evaluating perception intensity of an audio input signal according to claim 1, wherein said time variant distribution function is estimated by a shape description of a distribution function.

8. Method of evaluating perception intensity of an audio input signal according to claim 1, wherein said time variant distribution comprises an amplitude distribution function.

9. Method of evaluating perception intensity of an audio input signal according to claim 1, wherein said time variant distribution comprises a power distribution function.

10. Method of evaluating perception intensity of an audio input signal according to claim 1, wherein said time variant distribution comprises a sound intensity distribution function.

11. Method of evaluating perception intensity of an audio input signal according to claim 1, wherein said time variant distribution comprises a two-dimensional distribution function.

12. Method of evaluating perception intensity of an audio input signal according to claim 1, wherein the determining of the perception intensity estimate is made on the basis of at least two time variant distribution functions estimated at least two different times.

13. Method of evaluating perception intensity of an audio input signal according to claim 1, wherein an output sample is determined on the basis of a least two audio input samples.

14. Method of evaluating perception intensity of an audio input signal according to claim 1, wherein the determining the perception intensity is established on the basis of said estimated time variant distribution function according to at least one non-linear function.

15. Method of evaluating perception intensity of an audio input signal according to claim 14, wherein said at least one non-linear function is established by an artificial neural network.

16. Method of evaluating perception intensity of an audio input signal according to claim 15, wherein said artificial neural network comprises a multilayer perceptron.

17. Method of evaluating perception intensity of an audio input signal according to claim 14, wherein said at least one non-linear function is established by means of polynomial fitting.

18. Method of evaluating perception intensity of an audio input signal according to claim 14, wherein said at least one non-linear function is established by means of splining.

19. Method of evaluating perception intensity of an audio input signal according to claim 14, wherein the evaluation is established by a serial, a parallel or a combination thereof of at least two non-linear functions.

20. Method of evaluating perception intensity of an audio input signal according to claim 14, wherein said non-linear function is established on the basis of adaptation data.

21. Method of evaluating perception intensity of an audio input signal according to claim 1, wherein said perception intensity comprises loudness.

22. Method of evaluating perception intensity of an audio input signal according to claim 1, wherein said perception intensity comprises sharpness, annoyance, airiness, punchiness, brilliance, presence, fatness, deepness or edginess or any combination thereof.

23. Method of evaluating perception intensity of an audio input signal according to claim 1, wherein the estimation of said time variant distribution function is made on the basis of at least two different feature characterizing parameters of said audio input signal.

24. Method of evaluating perception intensity of an audio input signal according to claim 23, wherein at least one of said at least two different characterizing functions comprises a time variant statistical function.

25. Method of evaluating perception intensity of an audio input signal according to claim 23, wherein at least one of said feature characterizing parameters comprises a central value over time.

26. Method of evaluating perception intensity of an audio input signal according to claim 23, wherein at least one of said feature characterizing parameters comprises a measure of the spread over time, standard deviation, variance or inter quartile range.

27. Method of evaluating perception intensity of an audio input signal according to claim 23, wherein preprocessing of the audio input signal is done prior to the establishment of said at least two feature characterizing parameters.

28. Method of evaluating perception intensity of an audio input signal according to claim 1, wherein said time variant distribution function is determined in a time window.

29. Method of evaluating perception intensity of an audio input according to claim 1, wherein said audio input signal is modified on the basis of said evaluated perception intensity.

30. Method of evaluating perception intensity of an audio input signal according to claim 29, wherein said modifying of the audio input signal is performed as a gain control of the complete or a part of the audio input signal.

31. Method of evaluating perception intensity of an audio input signal according to claim 1, wherein said audio input signal comprises a multichannel signal.

32. Method of evaluating perception intensity of an audio input signal according to claim 1, wherein the perception intensity refers to a one-parameter evaluation of the audio input signal or a derivative thereof.

33. Method of evaluating perception intensity of an audio input signal according to claim 1, wherein the audio input signal or a derivative thereof is evaluated with respect to two or more different types of perception intensity and combinations thereof.

34. Method of evaluating perception intensity of an audio input signal according to claim 1, wherein said method is implemented in signal processing hardware comprising a digital signal processor and optional supporting electrical circuitry.

35. Method of evaluating perception intensity of an audio input signal according to claim 1, wherein said method results in automatic control of electronic circuitry.

36. Perception intensity estimating device comprising an audio signal input for receiving an audio input signal and signal processing circuitry performing the following steps:

estimating a time variant distribution function on the basis of said audio input signal or a derivative thereof;

determining the perception intensity as at least one perception intensity estimate on the basis of said estimated time variant distribution function;

establishing at least two different partial representations of the audio input signal, establishing at least two different statistical functions on the basis of at least one of said different partial representations of said audio input signal; and combining said determined statistical functions into a perception intensity representation by means of at least one non-linear signal processing.

37. Perception intensity estimating device according to claim 36 comprising monitoring means for displaying the estimated perception intensity.

38. Perception intensity estimating device according to claim 36 comprising control means for controlling connected electronic circuitry in response to the established perception intensity.

39. Method of evaluating perception intensity of an audio input signal comprising the steps of receiving the audio input signal;

estimating a time variant distribution function on the basis of said audio input signal or a derivative thereof;

determining the perception intensity as at least one perception intensity estimate on the basis of said estimated time variant distribution function, wherein the determining the perception intensity is established on the basis of the estimated time variant distribution function according to at least one non-linear function, the non-linear function being established on the basis of adaptation data.

40. Method of evaluating perception intensity of an audio input signal according to claim 39, wherein said estimating of a time variant distribution function is referring to the audio input signal.

41. Method of evaluating perception intensity of an audio input signal according to claim 39, wherein said estimating of a time variant distribution function is made on the basis of a modified audio input signal.

42. Method of evaluating perception intensity of an audio input signal according to claim 39, wherein said audio input signal comprises a sequence of input samples.

43. Method of evaluating perception intensity of an audio input signal according to claim 39, wherein said perception intensity estimate comprises an output sample.

44. Method of evaluating perception intensity of an audio input signal according to claim 43, wherein the determining of a perception intensity representative output sample is established on the basis of a weighted accumulation of at least two time variant distribution functions estimated at least two different times.

45. Method of evaluating perception intensity of an audio input signal according to claim 39, wherein said time variant distribution function is estimated by a shape description of a distribution function.

46. Method of evaluating perception intensity of an audio input signal according to claim 39, wherein said time variant distribution comprises an amplitude distribution function.

47. Method of evaluating perception intensity of an audio input signal according to claim 39, wherein said time variant distribution comprises a power distribution function.

48. Method of evaluating perception intensity of an audio input signal according to claim 39, wherein said time variant distribution comprises a sound intensity distribution function.

49. Method of evaluating perception intensity of an audio input signal according to claim 39, wherein said time variant distribution comprises a two-dimensional distribution function.

50. Method of evaluating perception intensity of an audio input signal according to claim 39, wherein the determining of the perception intensity estimate is made on the basis of at least two time variant distribution functions estimated at least two different times.

51. Method of evaluating perception intensity of an audio input signal according to claim 39, wherein an output sample is determined on the basis of a least two audio input samples.

52. Method of evaluating perception intensity of an audio input signal according to claim 39, wherein said at least one non-linear function is established by an artificial neural network.

53. Method of evaluating perception intensity of an audio input signal according to claim 52, wherein said artificial neural network comprises a multilayer perceptron.

54. Method of evaluating perception intensity of an audio input signal according to claim 39, wherein said at least one non-linear function is established by means of polynomial fitting.

55. Method of evaluating perception intensity of an audio input signal according to claim 39, wherein said at least one non-linear function is established by means of splining.

56. Method of evaluating perception intensity of an audio input signal according to claim 39, wherein the evaluation is established by a serial, a parallel or a combination thereof of at least two non-linear functions.

57. Method of evaluating perception intensity of an audio input signal according to claim 39, wherein said perception intensity comprises loudness.

58. Method of evaluating perception intensity of an audio input signal according to claim 39, wherein said perception intensity comprises sharpness, annoyance, airiness, punchiness, brilliance, presence, fatness, deepness or edginess or any combination thereof.

59. Method of evaluating perception intensity of an audio input signal according to claim 39, wherein the estimation of said time variant distribution function is made on the basis of at least two different feature characterizing parameters of said audio input signal.

60. Method of evaluating perception intensity of an audio input signal according to claim 59, wherein at least one of said at least two different feature characterizing parameters comprises a time variant statistical function.

61. Method of evaluating perception intensity of an audio input signal according to claim 59, wherein at least one of said feature characterizing parameters comprises a central value over time, such as a mean value, an average value or a median.

62. Method of evaluating perception intensity of an audio input signal according to claim 59, wherein at least one of said feature characterizing parameters comprises a measure of the spread over time, standard deviation, variance or inter quartile range.

63. Method of evaluating perception intensity of an audio input signal according to claim 59, wherein preprocessing of the audio input signal is done prior to the establishment of said at least two feature characterizing parameters.

64. Method of evaluating perception intensity of an audio input signal according to claim 39, wherein said time variant distribution function is determined in a time window.

65. Method of evaluating perception intensity of an audio input signal according to claim 39 including the steps of establishing at least two different partial representations of the audio input signal;

establishing at least two different statistical functions on the basis of at least one of said different partial representations of said audio input signal; and combining said determined statistical functions into a loudness representation by means of at least one non-linear signal processing.

66. Method of evaluating perception intensity of an audio input according to claim 39, wherein said audio input signal is modified on the basis of said evaluated perception intensity.

67. Method of evaluating perception intensity of an audio input signal according to claim 66, wherein said modifying of the audio input signal is performed as a gain control of the complete or a part of the audio input signal.

68. Method of evaluating perception intensity of an audio input signal according to claim 39, wherein said audio input signal comprises a multichannel signal.

69. Method of evaluating perception intensity of an audio input signal according to claim 39, wherein the perception intensity refers to a one-parameter evaluation of the audio input signal or a derivative thereof.

70. Method of evaluating perception intensity of an audio input signal according to claim 39, wherein the audio input signal or a derivative thereof is evaluated with respect to two or more different types of perception intensity and combinations thereof.

71. Method of evaluating perception intensity of an audio input signal according to claim 39, wherein said method is implemented in signal processing hardware, such as a digital signal processor and optional supporting electrical circuitry.

72. Method of evaluating perception intensity of an audio input signal according to claim 39, wherein the method results in automatic control of electronic circuitry.

73. Perception intensity estimating device comprising an audio signal input for receiving an audio input signal and signal processing circuitry performing the following steps:

estimating a time variant distribution function on the basis of said audio input signal or a derivative thereof; and determining the perception intensity as at least one perception intensity estimate on the basis of said estimated time variant distribution function;

determining the perception intensity as at least one perception intensity estimate on the basis of said estimated time variant distribution function, wherein the determining the perception intensity is established on the basis of the estimated time variant distribution function according to at least one non-linear function, the non-linear function being established on the basis of adaptation data.

74. Perception intensity estimating device according to claim 73 comprising monitoring means for displaying the estimated perception intensity.

75. Perception intensity estimating device according to claim 73 comprising control means for controlling connected electronic circuitry in response to the established perception intensity.

* * * * *